United States Patent [19]

Oswald et al.

[11] 4,298,541
[45] Nov. 3, 1981

[54] TRIHYDROCARBYL SILYL-SUBSTITUTED ALKYL DIARYL PHOSPHINE TRANSITION METAL COMPLEXES AND THEIR USE AS HOMOGENEOUS CATALYSTS

[75] Inventors: Alexis A. Oswald, Mountainside, N.J.; Torris G. Jermansen, Staten Island, N.Y.; Andrew A. Westner, Paramus; I-Der Huang, West Paterson, both of N.J.

[73] Assignee: Exxon Research & Engineering Co., Florham Park, N.J.

[21] Appl. No.: 11,238

[22] Filed: Feb. 12, 1979

[51] Int. Cl.$^3$ .............................................. C07F 15/00
[52] U.S. Cl. ........................... 260/429 R; 252/431 P; 260/439 R; 568/454
[58] Field of Search ........................ 260/429 R, 439 R

[56] References Cited

U.S. PATENT DOCUMENTS

| | | | |
|---|---|---|---|
| 3,067,229 | 12/1962 | Fekete | 260/448.2 |
| 3,122,581 | 2/1964 | Pike | 260/448.8 |
| 3,487,112 | 12/1969 | Paulik | 260/604 |
| 3,501,403 | 3/1970 | Jacques | 252/46.7 |
| 3,527,809 | 9/1970 | Pruett et al. | 568/454 |
| 3,726,809 | 4/1973 | Allum et al. | 260/448 C X |
| 3,832,404 | 8/1974 | Allum et al. | 260/429 R X |
| 3,856,837 | 12/1974 | Chandra | 260/429 R |
| 3,859,359 | 1/1975 | Keblys | 260/429 R X |
| 3,887,599 | 6/1975 | Chandra | 260/429 R |
| 3,890,359 | 6/1975 | Chandra | 260/429 R |
| 3,907,852 | 9/1975 | Oswald et al. | 260/429 R X |
| 4,052,461 | 10/1977 | Tinker et al. | 260/599 |
| 4,083,803 | 4/1978 | Oswald et al. | 252/430 |
| 4,108,905 | 8/1978 | Wilkinson | 260/604 HF |
| 4,134,906 | 1/1979 | Oswald et al. | 260/429 R X |

FOREIGN PATENT DOCUMENTS

| | | |
|---|---|---|
| 925721 | 5/1963 | United Kingdom . |
| 1182763 | 3/1970 | United Kingdom . |
| 1412257 | 10/1975 | United Kingdom . |
| 1414662 | 11/1975 | United Kingdom . |
| 1419769 | 12/1975 | United Kingdom . |
| 1420928 | 1/1976 | United Kingdom . |
| 1421136 | 1/1976 | United Kingdom . |

OTHER PUBLICATIONS

Brezezińska et al., Inorganic Chemistry, vol. 18, No. 11, pp. 3132 to 3138, (1979).
Jakoubková et al., Collection Czechoslov. Chem. Commun., vol. 45, pp. 2219-2223, (1980).
Cooper et al., J. Organometallic Chem., 29, 33-40, (1971).
Eaborn, Monograph on Organosilicon Compounds, Academic Press, Inc., N.Y., 1960, Table of Contents.
Discussions on "Homogeneous Catalysis", American Chemical Society Advances in Chemistry, Series 70, 1-24.
Falbe, Monograph on Carbon Monoxide in Organic Synthesis, Springer Verlag, NY, pp. 18-32, (1970).
O'Farrell et al., J. Organometal. Chem., vol. 169, pp. 199-208, (1979).
Chemtech, "Supported Homogeneous Catalysts", pp. 117-122, Feb. 1975.
Capka et al., Coll. Czech. Chem. Commun., vol. 43(12), pp. 334-335, Dec. 1978.
Pruett et al., Advances in Organometallic Chemistry, V17, p. 53, (1979).

*Primary Examiner*—Helen M. S. Sneed
*Attorney, Agent, or Firm*—A. H. Krumholz; Robert J. North

[57] ABSTRACT

Novel homogeneous trihydrocarbyl silyl-substituted alkyl diaryl phosphine transition metal complexes of the general formula:

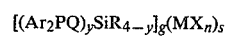

$$[(Ar_2PQ)_ySiR_{4-y}]_g(MX_n)_s$$

wherein Ar is a $C_6$ to $C_{10}$ aromatic hydrocarbyl radical, Q is a $C_1$ to $C_{30}$ saturated straight chain divalent radical either unsubstituted or substituted, R is an unsubstituted $C_1$ to $C_{10}$ hydrocarbyl, $C_1$ to $C_{10}$ monosubstituted hydrocarbyl, phenyl radical, y is 1 to 4, g times y is 1 to 6, M is a transition metal selected from the group consisting of Group VIII transition metals, X is an anion or organic ligand excluding halogen satisfying the coordination sites of the metal, n is 2 to 6 and s is 1 to 3, are disclosed. These materials are superior catalysts for the selective hydroformylation of olefins, particularly in the presence of excess quantities of the ligand of the formula:
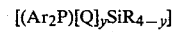
wherein Ar, Q, R, and y are as previously defined.
25 Claims, 2 Drawing Figures

TRIHYDROCARBYL SILYL-SUBSTITUTED ALKYL DIARYL PHOSPHINE TRANSITION METAL COMPLEXES AND THEIR USE AS HOMOGENEOUS CATALYSTS

DESCRIPTION OF THE ABSTRACT

Novel homogeneous trihydrocarbyl silyl-substituted alkyl diaryl phosphine transition metal complexes of the general formula:

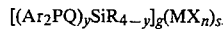

$[(Ar_2PQ)_y SiR_{4-y}]_g (MX_n)_s$ wherein Ar is a $C_6$ to $C_{10}$ aromatic hydrocarbyl radical, Q is a $C_1$ to $C_{30}$ saturated straight chain divalent radical either unsubstituted or substituted, R is an unsubstituted $C_1$ to $C_{10}$ hydrocarbyl, a $C_1$ to $C_{10}$ monosubstituted hydrocarbyl, phenyl radical, y is 1 to 4, g times y is 1 to 6, M is a transition metal selected from the group consisting of Group VIII transition metals, X is an anion or organic ligand excluding halogen satisfying the coordination sites of the metal, n is 2 to 6 and s is 1 to 3, are disclosed. These materials are superior catalysts for the selective hydroformylation of olefins, particularly in the presence of excess quantities of the material of the formula:

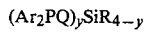

$(Ar_2PQ)_y SiR_{4-y}$ wherein Ar, Q, R, and y are as previously defined.

Specifically, tris-(trimethyl silyl-ethyl diphenyl phosphine) rhodium carbonyl hydride

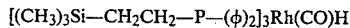

$[(CH_3)_3Si—CH_2CH_2—P—(\phi)_2]_3 Rh(CO)H$ is a selective butene-1 hydroformylation catalyst, particularly in the presence of excess trimethyl-silyl-ethyl disphenyl phosphine.

PRIOR ART

Transition metal complexes of both triphenyl phosphine and trialkyl phosphines are widely studied catalysts employed in hydroformylation, hydrogenation, etc., reactions. The monograph of Juergen Falbe, "Carbon Monoxide in Organic Synthesis," Springer Verlag, New York, 1970, deals with the use of these materials in reactions of carbon monoxide, particularly carbonylations. In the realm of rhodium catalyzed hydroformylations of α-olefins, catalyst systems of triaryl phosphine and other trivalent phosphorus compound rhodium complexes in the presence of excess phosphine ligand, which exhibited improved selectivity to normal aldehydes (over iso aldehydes), are described by R. L. Pruett and J. A. Smith in U.S. Pat. No. 3,527,809. In that patent, it is stated as being essential that the phosphorus ligands possess a half neutralization potential value at least 425, preferably at least 500 smaller than that of N,N' diphenylguanidine. The Δ HNP is only about 400, for simple alkyl diphenyl phosphines.

Morrell and Sherman in German Offenlegungsschrift No. 2,802,922 disclose unsubstituted alkyl diphenyl phosphines as components of stabilized tris-(triphenyl phosphine) rhodium carbonyl hydride plus excess triphenyl phosphine catalyst systems for hydroformylation of α simple olefins with CO/H$_2$ to give aldehydes.

In the area of silyl substituted alkyl phosphine transition metal complexes, the work of Grish Chandra is of importance. British Pat. Nos. 1,419,769; 1,420,928; 1,421,136 by Chandra disclose rhodium complexes of silyl alkyl phosphines, in each of which the rhodium had attached to it a halogen. These materials are disclosed as being useful for hydrosilylation, hydrogenation and hydroformylation. Specific examples are given only for the preparation of silylmethyl phosphine complexes and their use in hydrosilylation.

British Pat. Nos. 1,412,257; 1,414,662 and U.S. Pat. No. 3,856,837 (all to Chandra) describe nickel, palladium and platinum complexes of silylalkyl phosphines and their use of hydrosilylation, hydrogenation, and polymerization. In these patents, the transition metal has attached to it a halogen or —SCN group or —SZ wherein Z represents an alkyl radical having less than 18 carbon atoms or the phenyl radical.

In G.B. Pat. No. 1,412,257 the material is identified as a bridged binuclear complex.

In G.B. Pat. No. 1,414,662 the nickel, palladium or platinum transition group metal may have associated with it a hydrogen atom or other anionic ligand (X) which may be for example, H, Cl, Br, I, —NO$_2$, —NO$_3$, —SCH, —OCOCH$_3$, an alkyl, aryl, alkaryl or aralkyl radical. However, materials wherein X is Br are the only ones actually prepared.

In U.S. Pat. No. 3,856,837, the nickel, palladium or platinum also have preferably only halogens associated with them as anionic ligands (X).

G.B. Pat. No. 925,721 to H. Niebergall deals broadly with the addition of secondary phosphines to unsaturated silanes to provide silylhydrocarbyl phosphines. He discloses materials of the formula:

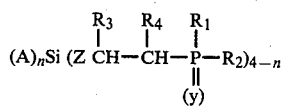

$$(A)_n Si \left( Z\; \underset{}{CH}\!-\!\underset{}{CH}\!-\!\underset{\underset{(y)}{\|}}{P}\!-\!R_2 \right)_{4-n}$$
$$\phantom{(A)_n Si \left( Z\; }R_3\;\;\;\;R_4\;\;\;R_1$$

wherein R$_1$ and R$_2$ are alkyl, cycloalkyl, aryl, alkaryl, aralkyl; R$_3$ and R$_4$ are alkyl, cycloalkyl, aryl, alkaryl, aralkyl or hydrogen; A is a halo, alkoxy, hydroxy, alkyl, alkaryl, cycloalkyl, aryl or aralkyl radical; Z is a hydrocarbon residue having from 1 to 10 carbon atoms and is preferably a saturated straight or branched chain hydrocarbon residue (or Z is a silicon to carbon linkage). If phosphorus is pentavalent, y is oxygen or sulfur; if phosphorus is trivalent, y is no substituent; n is 0 to 3. This patent contains no teaching that these materials can be complexed with transition metals to yield homogeneous catalysts useful in hydroformylation reactions.

Owen and Cooper disclose the preparation of similar compounds via displacement reactions of chlorophosphines and silylalkyl Grignard compounds or sodium phosphides and silylalkyl halides.

U.S. Pat. No. 3,067,227 to Fekete describes the preparation of alkoxysilylalkylphosphines via the method of reacting alkoxy silanes and unsaturated phosphines.

G.B. Pat. No. 1,182,763 to Jacques and Owen also disclose silylhydrocarbylphosphine intermediates useful in the preparation of the complexes of the present invention.

U.S. Pat. Nos. 3,726,809 and 3,832,404 to Allum et al disclose heterogeneous hydroformylation catalysts (and processes using these catalysts). These heterogeneous catalysts are silylhydrocarbyl phosphine transition metal complexes, bonded to a support by the interaction of a reactive group on the silicon with at least one reactive hydroxyl group on the support which may also be silicon. See also U.S. Pat. Nos. 3,907,852 and 4,083,803 to Oswald and Murrell.

THE INSTANT INVENTION

Composition

Figure 1:
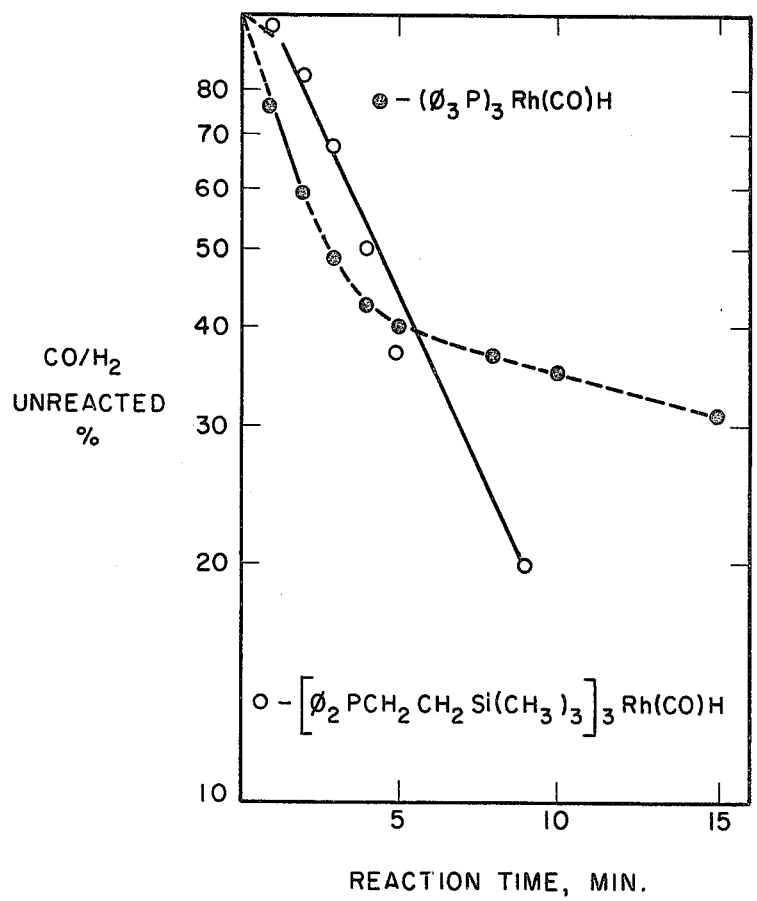
FIG. 1 represents a comparison of catalyst stabilities at high temperature hydroformylation of Butene-1. The catalysts compared are $(\phi_3P)_3RH(CO)H$ and $[\phi_2PCH_2Si(CH_3)_3]_3Rh(CO)H$.

The compositions of the present invention are hydrocarbylsilyl alkyl diaryl phosphine complexes of Group VIII transition metals free of metal bound halogen. They are represented by the formula:

$$[(Ar_2PQ)_ySiR_{4-y}]_g(MX_n)_s$$

wherein Ar is the same or different $C_6$ to $C_{10}$ substituted or nonsubstituted aromatic hydrocarbyl radical, preferably phenyl, mono-, di- or tri- substituted phenyl, most preferably phenyl; Q is a $C_1$ to $C_{30}$ saturated open chain alkylene radical, preferably a straight chain alkylene diradical, more preferably a $C_2$ to $C_{14}$ unsubstituted or monosubstituted alkylene diradical; R is the same or different $C_1$ to $C_{10}$ unsubstituted hydrocarbyl or $C_1$ to $C_{10}$ monosubstituted hydrocarbyl radical, preferably $C_1$ to $C_6$ alkyl, $C_5$ and $C_6$ cycloalkyl, phenyl, $C_1$ to $C_6$ monosubstituted alkyl, monosubstituted phenyl, more preferably $C_1$ to $C_6$ alkyl or phenyl, M is a Group VIII transition metal (Fe, Co, Ni, Pd, Pt, Rh, Ru, Ir, Oe) preferably Co, Rh, Ir, and Ru, more preferably Co, Rh, most preferably Rh; y is 1 to 4, preferably 1 or 2, most preferably 1; g times y is 1 to 6, preferably 1 to 4, more preferably 2 or 3, most preferably 3; X is an anion or organic ligand which satisfies the coordination sites of the metal, with the proviso that X cannot be halogen, preferably X is H, CO and tertiary phosphine, most preferably H, CO; n is 2 to 6, preferably 2; s is 1 to 3. Preferably all the organic radicals are unsubstituted.

Examples of Ar and aromatic R groups are naphthyl, fluorophenyl, mesityl, xylyl, acetylphenyl. Exemplary aliphatic R groups are methyl, hexyl, cyclohexyl, methyl; cyclopentyl, i-propyl, decyl, fluoropropyl, benzyl. Common Q alkylene groups are trimethylene, trimethylsilylethyl substituted ethylene, decamethylene, xylylene, octadecamethylene. The hydrocarbon bridging group between P and Si represented by Q may also be represented by $—(CH_2)_m$ wherein m ranges from 1 to 30, preferably 2 to 14.

Anions and organic ligands exemplified in the following: H-, alkyl-, aryl-, substituted aryl-, $CF_3^-$, $C_2F_5^-$, $CN^-$, $N_3^-$, where R is alkyl or aryl, acetate, acetylacetonate, $SO_4^{2-}$, $PF_4^-$, $NO_2^-$, $NO_3$, $O_2^-$, $CH_3O^-$, $CH_2=CHCH_2^-$, CO, $C_6H_5CN$, $CH_3CN$, NO, $NH_3$, pyridine, $(C_4H_9)_3P$, $(C_2H_5)_3N$, chelating olefins, diolefins and triolefins, tetrahydrofuran, $CH_3CN$, triphenyl phosphine. Preferred organic ligands are readily displaceable such as carbonyl, olefins, tetrahydrofuran, acetonitrile. Halogens may not be directly bonded to the transition metal.

Dependent on the subclass of the silylalkyl phosphine component used as an intermediate different types of the present complexes are derived:

$[Ar_2PQSiR_3]_go(MX_n)_s$; $g=1-6$; $y=1$ $[(Ar_2PQ)_2SiR_2]_go(MX_n)_s$; $2g=1-6$; $y=2$ $[(Ar_2PQ)_3SiR]_go(MX_n)_s$; $3g=1-6$; $y=3$ $[(Ar_2PQ)_4Si]_go(MX_n)_s$; $4g=1-6$; $y=4$

Among trihydrocarbylsilyl-alkyl phosphine rhodium complexes, preferred subgeneric classes are the following:

$[(Ar_2PQ)_ySiR_{4-y}]_g[Rh(CO)H]_s$ $[(Ar_2PQ)_ySiR_{4-y}]_3Rh(CO)H$ $(Ar_2PQSiR_3)_3Rh(CO)H$ $[(Ar_2PQSiR_3)_2Rh(CO)_3]^+[B\phi_4]^-$; $\phi=$phenyl $(ArPQSiR_3)_4Rh$ Some specifically preferred silylalkyl phosphine rhodium complexes possess short straight chain alkylene bridges Si and P $[(\phi_2P(CH_2)_m)_ySiR_{4-y}]_g[Rh(CO)H]_s$ Among the preferred examples of such compositions are the following:

$[\phi_2P(CH_2)_mSi(CH_3)_3]_3Rh(CO)H$ $[\phi_2P(CH_2)_mSi\phi_3]_3Rh(CO)H$ $\{[\phi_2P(CH_2)_m]_2Si(CH_3)_2\}_3[Rh(CO)H]_2$ $\{[\phi_2P(CH_2)_m]_3SiCH_3\}Rh(CO)H$ wherein m is 2 to 14, preferably 2 to 3 and wherein the complexes can be oligomeric whenever the silylalkyl phosphine has more than one phosphine group. $\phi$ is the $C_6H_5$ radical.

Examples of preferred types of complexes of other transition metals are:

$(\phi_2PQSiR_3)_3Co(CO)H$ $(\phi_2PQSiR_3)_3Ir(CO)H$ $(\phi_2PQSiR_3)Ru(CO)H$

Specific examples of the above are the following:

$[\phi_2PCH_2CH_2Si(CH_3)_3]_3Co(CO)H$ $[\phi_2PCH_2CH_2CH_2Si\phi_3]_3IR(CO)H$ $[\phi_2PCH_2Si(C_3H_7)_3]_3Ru(CO)H$

Preparation of Complexes and Silylalkyl Phosphine Intermediates Therefor

For the preparation of the present compositions, standard methods of organometallic chemistry synthesis are discussed in a comprehensive text, "Advanced Inorganic Chemistry" by F. A. Cotton and G. Wilkinson (Interscience Publishers, New York, 1972) and are exemplified in the series on "Inorganic Syntheses" particularly volume XV, edited by G. W. Parshall and published by McGraw-Hill Book Co., New York, 1974, and in U.S. Pat. No. 4,052,461 by H. B. Tinker and D. E. Morris.

For the preparation of the rhodium complexes, one of the specifically preferred direct method of synthesis starts with rhodium chloride. This method can be employed, e.g., for the synthesis of tris-(trihydrocarbylsilyalkyl diaryl phosphine) rhodium carbonyl hydride according to the following general scheme:

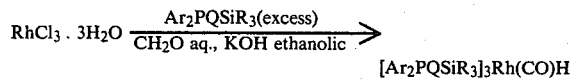

Other preferred direct methods of complex preparation include the reaction of transition metal carbonyls or oxides, such as those of rhodium with the silylalkyl phosphine ligand and CO/H$_2$. Similarly, organic salts of transition metals such as acetates can be reacted with the ligand.

The complexes can also be prepared via an indirect method by reaction of the corresponding complexes of a triaryl phosphine, preferably triphenyl phosphine, with the desired silylalkyl phosphine, preferably in excess, e.g.,

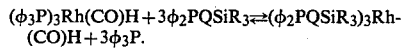

In general, the silylalkyl diaryl phosphine ligands are more basic than the corresponding triaryl phosphines. This basicity difference is a positive factor in the above ligand substitutions providing the novel, completely or partially exchanged complexes, e.g.,

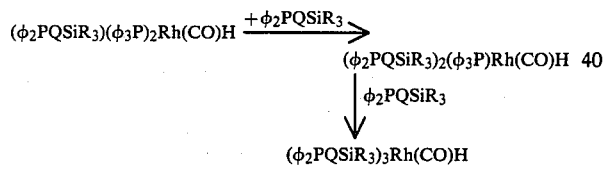

The intermediate silylalkyl phosphine ligands employed in the present invention are prepared by any number of standard techniques. U.S. Pat. Nos. 3,907,852 and 4,083,803 to Oswald and Murrell and G.B. Pat. No. 925,721 to Niebergall are representative of techniques which may be successfully employed to prepare the intermediates.

One preferred synthesis technique involves the addition of diaryl phosphines to unsaturated silanes:

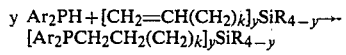

wherein k ranges from 0 to 28 and y ranges from 1 to 4. Such additions are preferably carried out via a radial mechanism in a free radical manner employing either chemical or radiation initiator. It is preferred that such reactions be conducted in the presence of from a 5 to 100% excess over the stoichiometric amount required to the phosphine. Use of this excess has been found to improve the selectivity of the process.

It has also been observed that additions of phosphines to vinylic silanes (k=O) occur with ease in the presence of radiation particularly ultraviolet light. The reactivity of the vinyl silanes is in marked contrast to the rather sluggish behavior of olefins having analogous structures. In addition to the vinyl silanes, allyl silanes (k=1) are another preferred class of reactant.

Another technique which may be employed in the preparation of the silyl hydrocarbyl phosphine intermediate involved in the present invention is the addition of silanes to unsaturated phosphines:

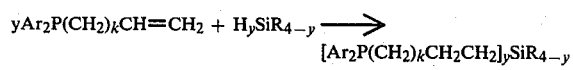

wherein k ranges from 0→28 and y ranges from 1→4.

These additions occur in an anti-Markovnikor manner via the mechanism discussed by C. Eaborn in the monograph "Organosilicon Compounds," Academic Press, Inc., Publishers, New York, 1960, and in the patent references previously identified. Again, the preferred reactants are the vinylic and allylic materials, this time the phosphines.

Other methods for silyalkyl phosphine preparation employ displacement reactions. One type of reaction starts with phosphides, particularly alkali metal phosphides, and chloro-, bromo-, or iodo-alkyl silanes:

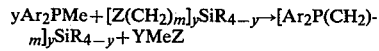

wherein Me is Na, K, Li; m is 1 to 30; Z is Cl, Br, I. Another technique starts with diaryl chloro or bromo phosphines and the corresponding Grignard derivatives of the silicon compounds:

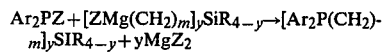

wherein Z is chlorine, bromine.

CARBONYLATION PROCESSES EMPLOYING HOMOGENEOUS SILYLALKYL PHOSPHINE-TRANSITION METAL COMPLEX CATALYSTS

It has been discovered that carbonylation reactions, particularly hydroformylation reactions, which involve the reaction of unsaturated organic compounds with CO, or CO and hydrogen mixtures can be successfully practiced in the presence of catalytically effective amounts of silyalkyl diaryl phosphine-Group VIII Transition metal complexes, preferably Co, Rh, Ir, Ru, Ni, Pt, Pd and mixtures thereof preferably Rh, Pd, Pt and mixtures thereof, most preferably Rh. Such complexes are preferably free of halogen directly associated with the metal. They preferably contain at least one of the silyalkyl diaryl phosphine ligand molecules per transition metal. It must be noted that the successful practice of the present invention does not depend on the exact structure of the catalytically active transient species, indeed, the exact structure is not known. In general, the complexes have three components, the Group VIII Transition metal, the hydrocarbyl silyalkyl diaryl phosphine ligand and a second ligand, X, selected from the group consisting of anions or organic ligands (preferably carbon monoxide) which satisfy the coordination sites of the metal with the proviso that theanion cannot be halogen when the metal is rhodium and preferably is not halogen even for the other Group VIII metals.

Carbonylation reactions are generally reactions of unsaturated organic compounds with carbon monoxide plus preferably a third reactant. Carbonylations are described in detail in the earlier referred Falbe monograph. Main types of cabonylations catalyzed by the present complexes are the Roelen reaction (hydroformylation) of olefins with CO and H₂ and subsequent aldolization reactions; the Reppe reaction (metal carbonyl catalyzed carbonylation) mainly of olefins, acetylenes, alcohols and activated chlorides with CO alone or with CO plus either alcohol or amine or water; and ring closure reactions of functional unsaturated compounds such as unsaturated amides with CO. The unsaturated organic reactants are preferably olefinically unsaturated compounds, more preferably olefinic hydrocarbons.

The carbonylations of the instant invention involve the use of catalysts of the general formula:

$$[(Ar_2PQ)_y SIR_{4-y}]_g o(MX_n)_s$$

wherein Ar, Q, y, g, M, X, n and s are as previously defined.

The most preferred carbonylation is an improved, selective hydroformylation comprising reacting an olefin with a mixture of carbon monoxide and hydrogen in the presence of a hydrocarbyl silylalkyl diaryl phosphine halogen free rhodium complex as a catalyst to produce mainly an aldehyde, preferably via carbonylation at the less substituted vinylic carbon.

The preferred catalysts for use in the instant process are complexes of Group VIII rows 1 and 2 (i.e., Fe, Co, Ru, Rh, Os, Ir) more preferably Rh, Co, Ru, Ir particularly Rh and Co. These complexes also should be preferably halogen free, i.e. X may not be halogen in the above general equation. The most preferred metal is rhodium. The most preferred catalysts are of the formula:

$$[((C_6H_5)_2P(CH_2)_m)_y SiR_{4-y}]_g[Rh(CO)H]_s$$

wherein m ranges from 1 to 30, preferably 2 to 14, most preferably 2 to 3; y ranges from 1 to 4, preferably 1 or 2, most preferably 1; R is $C_1$ to $C_6$ alkyl or phenyl, preferably methyl, ethyl, propyl or phenyl.

Specific preferred catalysts are:

$[(C_6H_5)_2P(CH_2)_m Si(CH_3)_3]_3 Rh(CO)H$ $[(C_6H_5)_2P(CH_2)_m Si(C_6H_5)_3]_3 Rh(CO)H$ $[[(C_6H_5)_2P(CH_2)]_2 Si(CH_3)_2]_3 [Rh(CO)H]_2$ $[[(C_6H_5)_2P(CH_2)]_3 Si(CH_3)] Rh(CO)H$.

Other specific preferred compounds employing different transition metals are:

$[(C_6H_5)_2P(CH_2)_2 Si(CH_3)_3]_3 Co(CO)H$ $[(C_6H_5)_2P(CH_2)_3 Si(C_6H_5)_3]_3 Ir(CO)H$ $[(C_6H_5)_2P(CH_2) Si(C_3H_7)_3]_3 Ru(CO)H$.

Particularly in the case of the rhodium complex hydroformylation catalysts, organic nonhydrocarbon solvents, preferably of weak, nonsubstituting ligand character, are advantageously used. Preferred solvents of ligand character are triaryl phosphines, such as triphenyl phosphine; triaryl stibines; triaryl arsines. Other preferred organic solvents are ketones such as acetophenone, diphenyl ketone; polyethylene glycol, organic silicone compounds such as diphenyl dipropyl silane. More preferred ligand solvents are triaryl phosphines. The most preferred solvent, however, is an excess of the same silylalkyl phosphine ligand which is complexed with the $(MX_n)_s$ group. In general, the preferred solvents, particularly the ligands, stabilize the catalyst system and increase its selectivity, particularly the ratio of linear versus branched products.

In case of continuous hydroformylations of $C_2$ to $C_6$ olefins, particularly ethylene wherein the volatile primary aldehyde reaction products are continuously removed, the nonvolatile secondary condensation products become the main solvents. Such inert, nonvolatile oxygenated organic solvents, preferably of carboxylic ester and alcohol character, are advantageously used. They are further improved by the presence of a ligand type phosphine.

The hydroformylation of olefins can be advantageously run in the present process in a manner coupling it with aldol condensation. For example, in the case of butene-1, the following conversions can be carried out in a combined process:

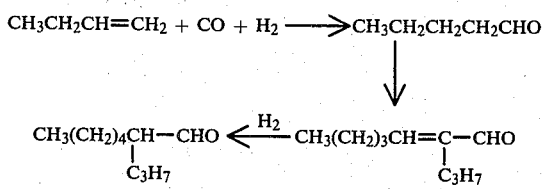

To realize such a conversion to an unsaturated or saturated aldol aldehyde, the present catalyst systems preferably contain added base such as KOH.

Carbonylation Process Conditions

The carbonylation processes catalyzed by the present silylalkyl phosphine catalysts can be carried out advantageously under the usual reaction conditions such as those described in the earlier referenced Falbe monograph. However, the reaction and particularly the rhodium complex catalyzed hydroformylation of olefinic compounds, preferably olefins in the 2 to 40 carbon range, especially olefinic hydrocarbons such as mono-, di- and triolefins is advantageously carried out within a certain set of special conditions.

The olefinic reactants of the present hydroformylation can be terminally or internally unsaturated and of open chain or cyclic structure. The internal olefins must contain at least one, preferably two, hydrogens on the vinylic carbons. Terminally olefinic reactants, particularly α-olefins are preferred. Among the most preferred olefin reactants are $C_2$ to $C_6$ olefins, i.e., propylene, butenes and pentenes, hexenes particularly propylene, butene-1 and pentene-1, and ethylene.

Exemplary diolefin reactants are divinyl cyclohexane and 1,7-octadiene. Di- and polyolefin reactants are preferably non-conjugated in character.

Substituted olefinic reactants can be also advantageously used as long as the substituent does not interfere with the catalyst system and is stable under the reaction conditions. Exemplary substituted olefins are allyl alcohol, methyl oleate, 3-butenyl acetate, diallyl ether, allyl chlorobenzene.

The preferred concentration of the transition metal complex catalysts and particularly the preferred rhodium complex catalysts is in the range of $1\times10^{-6}$ to $1\times10^{-1}$ mole metal per olefin reactant. More preferred concentrations are in the range of $1\times10^{-5}$ to $1\times10^{-1}$ and the most preferred range is $1\times10^{-4}$ to $1\times10^{-2}$. However, the preferred catalyst concentrations are directly affected by the concentration of free ligand present, especially the excess silylalkyl phosphine ligand. The higher the ligand concentration, the higher the metal level required for a certain reaction rate.

The preferred pressure range is from about 1 to 10,000 psi.

A preferred operation with the present rhodium complex catalysts includes the use of excess ligand, particularly silylalkyl phosphine. An excess of the ligand is employed, in spite of its adverse effect on reaction rates, mainly because its use results in higher catalyst selectivity and stability. In effect, the excess ligand affects the structure of the reactive catalyst species to provide these desired effects. In the case of -olefins, the use of excess ligand results in a higher ratio of linear versus isoaldehydes. For example, in the case of butene-1, hydroformylation a higher ratio of normal valeraldehyde to 2-methyl butyraldehyde is formed.

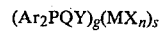

$$CH_3CH_2CH=CH_2 + CO + H_2 \longrightarrow$$
$$CH_3CH_2CH_2CH_2CHO + CH_3CH_2\underset{\underset{CH_3}{|}}{CH}CHO$$

The preferred mole ratio of excess ligand to transition metal complex varies from 0.1 to 500. Mole ratios ranging from 5 to 300 are more preferred. In general, higher mole ratios are required more for maximum selectivity than for stabilization. Higher ratios are also employed when the desired operation is a continuous rather than a batchwise operation.

The selectivity of the present rhodium complex hydrogenation catalysts also depends on the molar ratio of the gaseous CO and $H_2$ reactants. This $CO/H_2$ ratio should be below 1, preferably in the range of 0.5 to 0.005.

The preferred process conditions of the present rhodium complex catalyzed hydroformylations are unexpectedly mild. The preferred pressures are moderate; they are between 1 to 1000 psi. It is more preferred to operate between about 25 and 500 psi. The reaction temperatures are surprisingly low as far as hydroformylations are concerned. They are in the 25° to 200° C. range. Preferred temperatures are between 50° and 175° C. The broad operational temperature range is particularly unexpected. While high hydroformylation rates can be realized, for example at 100°, hydroformylations can be also effected at 145° without a catastrophic loss of normal/iso selectivity or loss of catalyst activity through decomposition.

The present process can be carried out either in the liquid or in the gaseous state. The catalysts can be employed as such or dissolved in a liquid or deposited but not bonded to a solid such as silica or alumina.

Particularly in the case of continuous process operation, the present carbonylations, especially the hydroformylation of terminal olefins, is advantageously carried out at a low olefin conversion, preferably at a 20 to 60% olefin conversion. In the preferred embodiment, low olefin conversion coupled with a high ligand to rhodium ratio results in a particularly high ratio of linear to branched products, generally higher selectivity and improved catalyst stability, i.e., catalyst life.

Other novel substituted alkyl diaryl phosphine transition metal complexes which can be used as carbonylation catalysts (either as such or in the presence of excess substituted alkyl diaryl phosphine ligands or other non-exchanging ligands or solvents) are represented by the general formula:

$$(Ar_2PQY)_g(MX_n)_s$$

wherein Ar is a $C_6$ to $C_{10}$ substituted or unsubstituted aromatic radical, Q is a $C_1$ to $C_{30}$ unsubstituted or substituted saturated straight chain divalent radical, Y is an organic substituent having a higher steric requirement than methylene or polymethylene, such as quaternary tetraalkyl phosphonium; heterocyclic tertiary nitrogen; phosphine oxide; sulfone groups; carbonyl and carboxylate groups and sterically demanding hydrocarbon groups such as phenyl, triphenylmethyl, t-butyl, tris-hydroxy substituted t-butyl, etc.; g is 1 to 3; M is a transition metal selected from Group VIII; X is an anion or organic ligand satisfying the coordination sites of the metal; n is 2 to 6 and s is 1 to 3.

EXAMPLES

Example 1

Preparation of Trimethylsilylethyl Diphenyl Phosphine

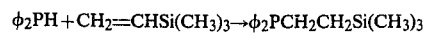

$$\phi_2PH + CH_2=CHSi(CH_3)_3 \rightarrow \phi_2PCH_2CH_2Si(CH_3)_3$$

A magnetically stirred mixture of 46.5 g (0.25 mole) diphenyl phosphine and 25 g (0.25 mole) of vinyl trimethyl silane, in a closed cylindrical quartz tube, was irradiated from about 3 cm distance with two 75 Watt Hanau tube immersion lamps, with a wide spectrum of ultraviolet irradiation, in a 15° C. water bath for 26 hours. A proton magnetic resonance spectrum of a sample of the resulting mixture exhibited no significant peaks in the vinyl region indicating a substantially complete addition.

The reaction mexture was distilled in vacuo to obtain 61 g (81%) of the desired trimethylsilylethyl diphenyl phosphine adduct, as a clear colorless liquid, having a boiling range of 109°–110° at 0.1 mm.

Anal. Calcd. for $C_{17}H_{23}PSi$: C, 71.29; H, 8.09; P, 10.81. Found: C, 71.98; H, 8.12; P, 10.59.

The selectivity to provide the desired adduct was increased when the diphenyl phosphine reactant was employed in a 10 mole % excess.

Example 2

Preparation of Tris (Trimethylsilylethyl Diphenyl Phosphine) Rhodium Carbonyl Hydride

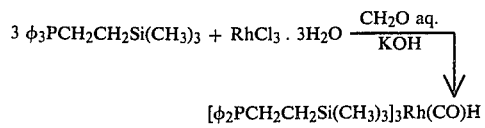

$$3\ \phi_3PCH_2CH_2Si(CH_3)_3 + RhCl_3 \cdot 3H_2O \xrightarrow[KOH]{CH_2O\ aq.}$$
$$[\phi_2PCH_2CH_2Si(CH_3)_3]_3Rh(CO)H$$

To a vigorously stirred, refluxing, nitrogenated solution of 11.44 g (40 mmole) of tris-(trimethylsilylethyl) diphenyl phosphine of Example 1 in 400 ml of ethanol, a hot solution of 1.04 g (0.4 mmole) of rhodium trichloride trihydrate in 80 ml ethanol was added at once. After a delay of 15 seconds, 40 ml warm aqueous (37%)

formaldehyde solution and, immediately thereafter, 80 ml hot ethanolic solution of 3.2 g of potassium hydroxide were added. The resulting clear orange liquid reaction mixture was refluxed for 10 minutes. During the heating, the color changed to deep orange.

The mixture was cooled to $-25°$ C. to crystallize the complex product. Crystallization started at $-10°$ C. and was completed on standing for about 2 hours at $-25°$ C. The crystalline complex was separated by filtration through a precooled Buechner funnel with suction and washing successively with 20 ml cold portions of ethanol, water, ethanol and n-hexane. The complex was then dried in the presence of anhydrous calcium chloride at 0.1 mm over the weekend. As a result, 2.2 g (2.2 mmol 55%) of dry tris-(trimethylsilylethyl diphenyl phosphine) rhodium carbonyl hydride complex was obtained as a fine crystalline orange-yellow powder. In a sealed capillary tube, the complex melted between 126°–129° C. to a clear dark red liquid. In an open capillary, complete melting occurred at 121°. There was no sign of decomposition on heating up to 140° in either case.

The infrared spectrum of the complex in Nujol showed a strong carbonyl band of 1985 cm$^{-1}$ and a band of medium intensity at 1900 cm$^{-1}$.

Analyses Calcd. for $C_{52}H_{70}OP_3RhS$: C, 63.01; H, 7.12; P, 9.38; Found: C, 62.89; H, 7.06; P, 9.59.

General Method of Hydroformylation

The hydroformylation of butene-1 to provide linear pentanal and branched 2-methyl butanal products was selected for comparative studies of the catalytic properties of the novel tris-(trihydrocarbylsilyl-alkyl diphenyl phosphine) rhodium carbonyl hydride complexes. The complexes studied were either isolated before use or generated in situ from the known tris-(triphenyl phosphine) rhodium carbonyl hydride by the addition of the appropriate novel ligand in varying amounts. Tris-(triphenyl phosphine) rhodium carbonyl hydride in the presence of varying excess of triphenyl phosphine was used as a known catalyst standard for comparison.

The experiments were carried out in a 300 ml stainless steel (S) and a 300 ml Hastalloy (H) autoclave, respectively. Both autoclaves were equipped with identical, highly effective, impeller type stirrers, operating at 750 rpm during the experimental runs. The other standard autoclave instrumentation was identical for both units. However, a slightly lower normal to iso aldehyde product ratio (n/i) was observed in unit H.

The standard hydroformylation procedure was the following: the appropriate amounts of rhodium complex were dissolved in 100 g of the proper mixture of free phosphine and 2-propyl heptyl n-valerate solvent. Most often the amount of complex employed provided 100 ppm rhodium concentration. This meant 100 mg, i.e., about 0.1 mmole rhodium per 100 g. Accordingly, 100 mg per kg, about 1 mmole per kg rhodium would be present in 1 kg starting mixture. The excess ligand added to the solvent was calculated to provide a ligand to rhodium ratio (L/Rh) in the 5 to 140 range.

The 100 g rhodium complex-ligand solution was placed into the autoclave which was then deaerated by repeated pressurization with nitrogen. The solution under atmospheric nitrogen pressure was then sealed and heated to the reaction temperature, usually 100° C.

When the solution reached 100°, 20 g liquid butene was pressured into the autoclave with a 1 to 4 carbon monoxide-hydrogen mixture. The butene was followed by the CO/H$_2$ mixture until a pressure of 350 psig was reached. At that point, the supply of 1:4 CO/H$_2$ was shut off and the autoclave was connected to a cylinder of about 1 liter volume containing a 1:1 CO/H$_2$ mixture at 1000 psig. The connection was made through a pressure regulating valve set to provide the 1:1 CO/H$_2$ gas to the autoclave to maintain a 350 psig pressure during the reaction.

The progress of the hydroformylation was followed on the basis of the amount of 1:1 CO/H$_2$ consumed. The latter was calculated on the basis of the pressure drop in the 1 liter CO/H$_2$ cylinder. Reactant conversion calculated on the basis of CO consumption was plotted against the reaction time to determine the reaction rate. The reaction rate was expressed as the fraction of the theoretical CO/H$_2$ requirement consumed per minute (k min$^{-1}$). The reaction was discontinued when the reaction rate drastically dropped. Depending on the side reaction, such as butene-1 hydrogenation and butene-1 to butene-2 isomerization, the stability of the catalyst complex in the mixture, such a rate drop occurred generally between 80–98% CO conversion. Accordingly, the reactions were usually discontinued in that conversion range. When the reaction was to be discontinued, the CO/H$_2$ feed valve was shut and the autoclave was immediately cooled with cool water. In case of low conversions, ice bath was used. When cooling was complete, the synthesis gas was released slowly. The residual liquid was visually observed for catalyst decomposition. A dark orange to brown color of the originally yellow mixture indicated increasing degrees of catalyst decomposition. Severe catalyst decomposition usually resulted in the precipitation of dark solids.

Analyses of the residual liquid mixture were carried out using gas chromatography. The liquids were analyzed in a gc instrument using flame ionization detector. By this instrument, the C$_4$ hydrocarbons were detected and measured as a single peak. The two isomeric C$_5$ aldehydes were completely separated. The ester solvent and the ligands were also clearly detected. Due to the lower response of this detector to the aldehydes, the intensity of the hydrocarbon peaks was multiplied usually by 0.7 to obtain the necessary concentration correction. The individual, gaseous C$_4$ hydrocarbons were separated by another chromatograph. These gases were separated from the liquids and then the individual components of the gas were chromatographed and detected by a thermal conductivity detector.

Hydroformylation Experiments

Example 3

Tris-(Trimethylsilylethyl Diphenyl Phosphine) Rhodium Carbonyl Hydride as a Catalyst in the Presence of 140-Fold Ligand Excess at Different Temperatures The complex of Example 2 was studied at the 107 ppm rhodium level in the presence of 140-fold trimethylsilylethyl diphenyl phosphine (SEP) ligand as a butene hydroformylation catalyst using the general procedure. Comparative experiments were run using 107 ppm rhodium as a tris-(triphenyl phosphine) carbonyl hydride complex with 140-fold triphenyl phosphine (TPP). Reaction rates, n/i product ratios, conversions and by-products were determined at various temperatures. The results are shown by Table I.

The data of the table show that both the SEP and the TPP based catalyst systems are highly active and produce a high ratio of i/n products at most temperatures. However, the temperature dependence of the two systems is very different.

trimethylsilylethyl diphenyl phosphine ligand (SEP). The SEP concentration used ranged from 5 to 149 mmole per liter. Some comparative experiments were

TABLE I

HYDROFORMYLATION AT DIFFERENT TEMPERATURES

Feed: Butene-1 and 1:4 $CO/H_2$ at 350 psi
Catalyst: $L_3Rh(CO)H$, Rh 107 ppm, L/Rh = 140
SEP Ligand: $(CH_3)_3SiCH_2CH_2P\phi_2$
TPP Ligand: $\phi_3P$

| | Variable Conditions of Catalysis | | Reaction Rates and Selectivities | | | By-Product, Mole % in Product Mixture | | Details | |
|---|---|---|---|---|---|---|---|---|---|
| Seq. No. | Catalyst Ligand | Reaction Temp., °C. | Fraction of $CO/H_2$ Reacted k, min$^{-1}$ | Product n/i Ratio | Reaction Time Min. | Butene Conversion % | Butane | Butene-2 | Exact Rh Conc. ppm | Exp. Run No. |
| 1 | SEP | 100 | 0.03 | 6.1 | 35 | 86.9 | 2.0 | 3.8 | 106 | 104 |
| 2 | | 120 | 0.10 | 6.2 | 35 | 96.5 | 9.4 | 6.2 | 106 | 110 |
| 3 | | 140 | 0.21 | 5.7 | 15 | 97.5 | 14.5 | 12.4 | 108 | 109 |
| 4 | | 145 | 0.27 | 5.0 | 15 | 95.2 | 11.9 | 12.1 | 109 | 115 |
| 5 | TPP | 100 | 0.21 | 7.5 | 35 | 98.9 | 10.7 | 12.1 | 107 | 100 |
| 6 | | 120 | 0.34 | 5.9 | 10 | 97.3 | 9.3 | 12.2 | 104 | 112 |
| 7 | | 140 | 0.38 (A,B) | 3.4 | 10 | 98.2 | 11.2 | 21.9 | 105 | 113 |
| 8 | | 145 | 0.27(A,C) | 2.4 | 15 | 97.7 | 11.9 | 26.0 | 103 | 114 |

A - this value of rate constant was determined on the basis of the first four minutes of the reaction.
B - after four minutes the "rate constant" drops to 0.01.
C - after four minutes the "rate constant" abruptly drops to 0.002.

The novel SEP catalyst system exhibits an increasing activity with elevated temperatures. At 100° and 120° the n/i ratio of products is about the same and there is only a small n/i drop at 145°. High butene conversion is observed at all temperatures. The only adverse effect of temperature increase is in the increased hydrogenation and isomerization of the butene-1 reactant. The SEP system remains clear, bright yellow in appearance, even at 145°.

The known TPP catalyst system exhibits the same increased activity at 120° and 140°. However, the n/i ratios in this case are dramatically reduced with increasing temperatures. At 145°, the n/i ratio products is significantly lower in the TPP than in the SEP system. At 145°, the reaction rate of the TPP system also drops. Decomposition of this system at this temperature is indicated by abrupt kinetic rate changes, as shown by FIG. 1.

Example 4

Tris-(Trimethylsilylethyl Diphenyl Phosphine) Rhodium Carbonyl Hydride as a Catalyst at Different Levels of Excess Ligand Concentrations

The complex catalyst of Example 2 was studied mainly at the 105 ppm rhodium level and at 100° reaction temperature to determine the effect of the excess also carried out using tris-(triphenyl phosphine) rhodium carbonyl hydride and varying excess concentrations of the corresponding triphenyl phosphine ligand (TPP). The results of these studies are shown in Table II.

Figure 2:
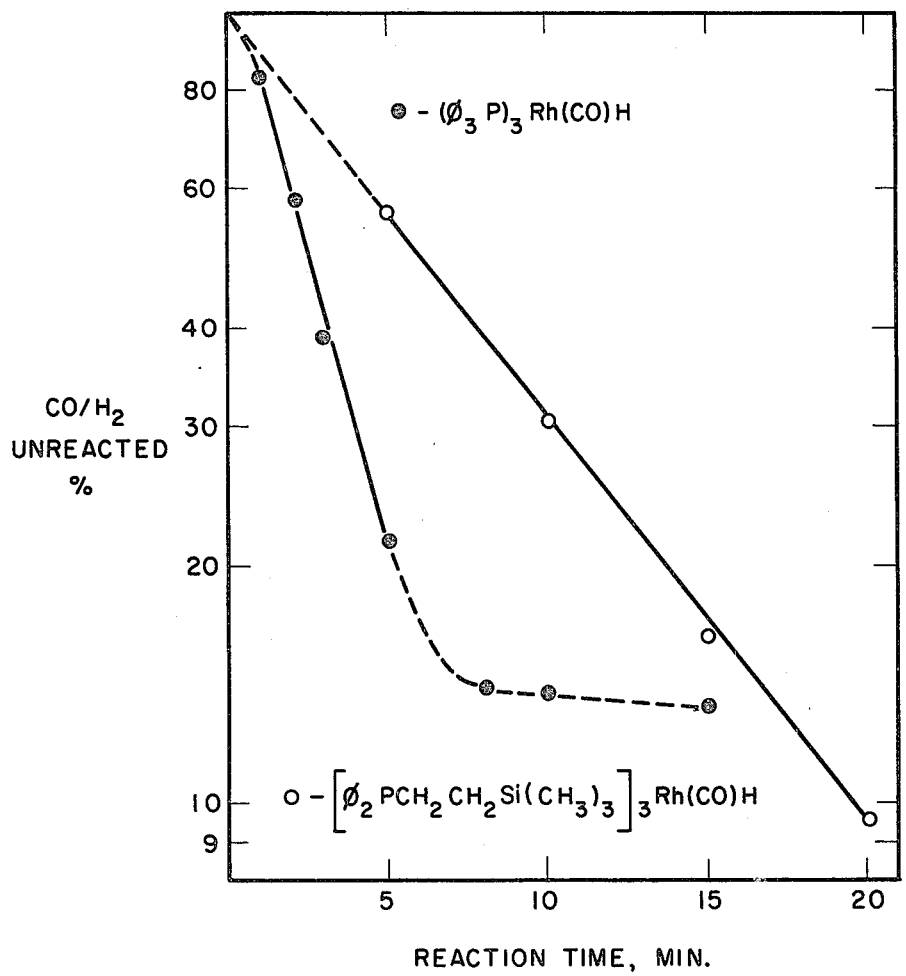
FIG. 2 presents a comparison of catalyst stability at low ligand/rhodium ratios for hydroformylation of Butene-1. The catalysts compared are $(\phi_3P)_3Rh(CO)H$ and $[\phi_2PCH_2CH_2Si(CH_3)_3]_3Rh(CO)H$.

The data of Table II show that, in general, increasing concentrations of excess ligand result in decreased reaction rates but sharply increased selectivities, i.e., n/i ratios, in both the novel and the known catalyst systems. There is an apparent inhibition and stabilization of both systems at high ligand concentrations. However, the behavior of the two catalysts is significantly different at relatively low excess ligand concentrations, as shown in FIG. 2.

The percentages of unreacted $CO/H_2$ with volume corrections were plotted against the reaction time in the case of the experiments of sequences number 3 and 11 of Table II. The resulting curves for the SEP and TPP catalyst systems indicate that initially the use of the TPP catalyst system results in a higher reaction rate. Then a drastic reduction of conversion rate occurs. In contrast, the slower reaction rate of the SEP catalyst system is maintained. This shows the superior stability of this catalyst at the relatively moderate L/Rh ratio used (27).

TABLE II

HYDROFORMYLATION AT DIFFERENT LEVELS OF EXCESS LIGAND CONCENTRATIONS

Feed: Butene-1 and 1:4 $CO/H_2$ at 350 psi
Catalyst: $L_3Rh(CO)H$
SEP Ligand: $(CH_3)_3SiCH_2CH_2P\phi_2$
TPP Ligand: $\phi_3P$

| | Variable Conditions of Catalysis | | | | | | Reaction Rates and Selectivities | | | |
|---|---|---|---|---|---|---|---|---|---|---|
| Seq. No. | Catalyst Ligand | Reaction Temp., °C. | Auto-Clave | Excess Ligand Conc. mMole/lit. | Rhodium Conc. ppm | Ligand to Rh Ratio L/Rh | Fraction of $CO/H_2$ Reacted k min$^{-1}$ | Product Linearity Ratio, n/i | Reaction Time min. | CO Conversion 90 |
| 1 | SEP | 100 | H | 5 | 105 | 5.2 | 0.24 | 3.5 | 20 | 88.7 |
| 2 | | | | 24 | 105 | 24.2 | 0.09 | 4.0 | 35 | 87.1 |
| 3 | | | S | 28 | 105 | 28 | 0.12 | 4.4 | 35 | 88.0 |
| 4 | | | | 56 | 217 | 28 | 0.12 | 5.4 | 30 | 94.2 |
| 5 | | | | 143 | 105 | 143 | 0.03 | 6.1 | 35 | 83.6 |
| 6 | | 120 | S | 29 | 105 | 29 | 0.30 | 4.5 | 15 | 93.0 |
| 7 | | | | 60 | 210 | 30 | 0.25 | 5.7 | 15 | 89.6 |
| 8 | | | | 149 | 105 | | 0.10 | 6.2 | 35 | 88.1 |
| 9 | TPP | 100 | H | 5 | 105 | 5 | 0.28 | 3.0 | 15 | 80.8 |
| 10 | | | | 142 | 102 | 142 | 0.17 | 3.8 | 35 | 96.5 |

TABLE II-continued
HYDROFORMYLATION AT DIFFERENT LEVELS OF EXCESS LIGAND CONCENTRATIONS Feed: Butene-1 and 1:4 $CO/H_2$ at 350 psi
Catalyst: $L_3Rh(CO)H$
SEP Ligand: $(CH_3)_3SiCH_2CH_2P\phi_2$
TPP Ligand: $\phi_3P$

| | Variable Conditions of Catalysis | | | | | Reaction Rates and Selectivities | | | |
|---|---|---|---|---|---|---|---|---|---|
| Seq. No. | Catalyst Ligand | Reaction Temp., °C. | Auto-Clave | Excess Ligand Conc. mMole/lit. | Rhodium Conc. ppm | Ligand to Rh Ratio L/Rh | Fraction of $CO/H_2$ Reacted $k\ min^{-1}$ | Product Linearity Ratio, n/i | Reaction Time min. | CO Conversion 90 |
| 11 | | | S | 27 | 105 | 27 | 0.31 | 4.7 | 15 | 86.6 |
| 12 | | | | 143 | 104 | 143 | 0.03 | 6.1 | 35 | 83.6 |

The novel SEP catalyst system leads to higher n/i product ratio than the TPP system at five mmole/l excess ligand concentration (Seq. No. 1 vs. Seq. No. 9). At the intermediate SEP concentration of 56 mmole, there is a good selectivity and sufficient reaction rate (Seq. No. 4). It is interesting to observe that the positive effect of increasing catalyst complex concentration on the reaction rate can be counter-balanced by negative effect of increased SEP concentration (compare Seq. Nos. 3 vs. 4 and 6 vs. 7). Clearly, the SEP concentration is more important than the SEP/Rh ratio. At the high SEP level of 143, there is some further increase in the n/i ratio, but reaction rate is cut to about one fourth (compare Seq. Nos. 4 and 5). At this level, the rate can be increased while maintaining the high n/i ratio by increasing the reaction temperature (see Seq. No. 8 and the table of the previous example).

Example 5

Hydroformylation Selectivity of Tris-(Trimethylsilylethyl Diphenyl Phosphine) Rhodium Carbonyl Hydride Excess Ligand Catalyst System at Different Butene-1 Concentrations Butene-1 was hydroformylated in the Hastalloy unit according to the general procedure. The catalyst and ligand concentrations were higher than usual and the reaction conditions milder as shown in Table III. The reaction mixture was frequently sampled during the process and the samples were analyzed by gc to determine the relative selectivities to n- and i-aldehyde products and hydrocarbon by-products as a function of butene-1 conversion. The detailed data are given in Table III.

The data of Table III indicate that the n- to i-ratio of aldehydes in the reaction is decreasing as the conversion increases. Up to about 60% butene conversion, the n/i ratio stays above 18.5, although it is steadily dropping (see Sample Nos. 1-3). In the 72-78% conversion range, the n/i ratio is about 14. Once butene-1 conversion reaches 90%, the n/i ratio of the product mixture is down to about 11.5

TABLE III
HYDROFORMYLATION SELECTIVITY AT DIFFERENT OLEFIN CONVERSION LEVELS

Feed: Butene-1 and 1:4 $CO/H_2$ at 130 psi at 110° C. under 130 psi
Catalyst: $L_3RH(CO)H$, Rh 212 ppm, L Excess 300 mMole, L/Rh 140
L: $\phi_2PCH_2CH_2Si(CH_3)_3$

| | Conversion Related Data | | | Aldehyde Product Linearity Ratio, n/i | Mole % Selectivity to Various Compounds | | | | |
|---|---|---|---|---|---|---|---|---|---|
| Sample No. | Butene-1 Conversion % | Conversion, % Based on $CO/H_2$ Consumed | Reaction Time, Min. | | Aldehyde Products | | Butane Hydrogenation Product | 2-Butene By-Products | |
| | | | | | n | i | | cis | trans |
| 1 | 26.4 | 21.9 | 10 | 26 | 68.4 | 2.7 | 11.9 | 9.7 | 7.3 |
| 2 | 46.9 | 36.0 | 15 | 25 | 77.9 | 3.1 | 7.4 | 6.7 | 4.9 |
| 3 | 61.6 | 50.0 | 20 | 18.5 | 79.7 | 4.3 | 6.1 | 5.8 | 4.2 |
| 4 | 72.0 | 61.4 | 25 | 13.9 | 80.2 | 5.8 | 5.2 | 5.2 | 3.7 |
| 5 | 78.0 | 69.4 | 30 | 14.0 | 79.6 | 5.7 | 5.4 | 5.4 | 3.9 |
| 6 | 90.0 | 79.9 | 40 | 11.6 | 82.1 | 7.1 | 3.9 | 4.0 | 2.9 |
| 7 | 90.5 | 87.9 | 60 | 11.3 | 81.9 | 7.2 | 4.0 | 4.0 | 3.0 |

It was also observed that during the conversion of about 25% of the butene, the total aldehydes to hydrocarbon by-products ratio was lower than at higher conversions (about 70/30 versus 90/10). It is believed that this is due to uncontrolled nonequilibrium conditions early during the reaction. Almost all the hydrogenation occurred during the first 10 minutes of the reaction. High selectivity to aldehydes at very low conversions can be achieved in a continuous process.

Hydroformylation with Exchanging Ligand Systems

In a series of experiments, tris-(triphenyl phosphine) rhodium carbonyl hydride was reacted with a verying excess concentration of the novel substituted alkyl diphenyl alkyl phosphines. This resulted in the formation of the novel catalysts of the present invention which were studied for their catalytic properties in the usual manner in the Hastalloy unit (H).

Example 6

Hydroformylation with the Tris-(Trimethylsilylethyl Diphenyl Phosphine) Complex System Tris-(triphenyl phosphine) rhodium carbonyl hydride, 0.1 g (0.1 mmole), was mixed with 80 g of a mixture of 4 g (14 mmole) of trimethylsilylethyl diphenyl phosphine and 76 g 2-propylheptyl valerate to provide a SEP catalyst system. For comparison, the same complex was also mixed with 80 g of a mixture of 3.7 g (14 mmole) of triphenyl phosphine to provide a TPP catalyst system. This provided two systems having 105 ppm rhodium and a 140 fold ligand excess.

Butene hydroformylations were then carried out with both catalyst systems at 100° in the usual manner. The results indicated that the main catalytic species of the SEP system is a SEP complex. The reaction rate of the SEP system was about 1/6 of the TPP system (K min$^{-1}$ values of 0.02 and 0.12, respectively). The n/i product ratios were about the same (4.2).

Other SEP catalyst systems were made up the same way except for the different L/Rh ratios: 25 and 5. They were also employed successfully for butene hydroformylation.

Example 7

Hydroformylation of Propylene in the Presence of Tris-(Trimethylsilylethyl Diphenyl Phosphine) Rhodium Carbonyl Hydride and Excess Ligand The complex of Example 2 was studied at the 458 ppm rhodium level, in the presence of a one hundred fold excess of trimethylsilylethyl diphenyl phosphine ligand, as a propylene hydroformylation catalyst. The reaction temperature was 110°, the 1:4 CO/H$_2$ pressure was 400 psi. The general procedure previously employed for butene hydroformylation was used to carry out the reaction.

The reaction rate was found to be k=0.04 min$^{-1}$, expressed as the fraction reacted. In 60 minutes, 82% conversion was reached based on the CO/H$_2$ consumed. The ratio of n-butyraldehyde to methyl-propanal products was 5.0. The selectivity to these aldehydes was 87.5%. The selectivity to the by-product propane was only 2.5%.

What is claimed is:

1. Complexes of the formula:

$$[(Ar_2PQ)_y SiR_{4-y}]_g (MX_n)_s$$

wherein Ar is selected from phenyl and mono-, di- or trisubstituted phenyl, said substituents being selected from the group consisting of fluorine, methyl and acetyl; Q is selected from xylylene and a C$_2$–C$_{14}$ straight chain alkylene divalent radical; R is a C$_1$ to C$_6$ hydrocarbyl radical selected from the group consisting of C$_1$ to C$_6$ alkyl, C$_5$ and C$_6$ cycloalkyl, and phenyl; M is a Group VIII transition metal selected from the group consisting of Co, Rh, Ir, Ru,; X is an anion or organic ligand, excluding halogen, satisfying the coordination sites of the metal; y is 1 to 4; g is 1 to 6 with the proviso that g times y is 1 to 6; n is 2 to 6; and s is 1 to 3.

2. Complexes of claim 1, wherein M is Rh.
3. Complexes of claim 2, wherein Ar is phenyl.
4. Complexes of the formula $$[(Ar_2PQ)_y SiR_{4-y}]_g [Rh(CO)H]_s$$

wherein Ar is selected from phenyl and mono-, di- or tri-substituted phenyl, said substituents being selected from the group consisting of fluorine, methyl and acetyl; Q is selected from a xylylene and C$_2$ to C$_{14}$ straight chain alkylene divalent radical; R is a C$_1$ to C$_6$ hydrocarbyl radical selected from the group consisting of C$_1$ to C$_6$ alkyl, C$_5$ and C$_6$ cycloalkyl, and phenyl; y is 1 to 4; g times y is 1 to 6; and s is 1 to 3.

5. Complexes of the formula $$(Ar_2PQSiR_3)_3 Rh(CO)H$$

wherein Ar is selected from phenyl and mono-, di- or tri-substituted phenyl, said substituents being selected from the group consisting of methyl, fluorine and acetyl; Q is selected from xylylene and a C$_2$ to C$_{14}$ straight chain alkylene divalent radical; and R is C$_1$ to C$_6$ hydrocarbyl radical selected from the group consisting of C$_1$ to C$_6$ alkyl, C$_5$ and C$_6$ cycloalkyl, and phenyl.

6. Complexes of claim 4 or 5 wherein, Ar is phenyl.
7. Complexes of the formula $$[(Ar_2PQSiR_3)_2 Rh(CO)_3]^+ [B(C_6H_5)_4]^-$$

wherein Ar is selected from phenyl and mono-, di- or tri-substituted phenyl, said substituents being selected from the group consisting of fluorine, methyl and acetyl; Q is selected from a xylylene and a C$_2$ to C$_{14}$ straight chain alkylene divalent radical; and R is a C$_1$ to C$_6$ hydrocarbyl radical selected from the group of C$_1$ to C$_6$ alkyl, C$_5$ and C$_6$ cycloalkyl, and phenyl.

8. Complexes of claim 7, wherein Ar is phenyl.
9. Complexes of the formula $$[(\phi_2 P(CH_2)_m)_y SiR_{4-y}]_g [Rh(CO)H]_s$$

wherein R is a C$_1$ to C$_6$ hydrocarbyl radical selected from the group of C$_1$ to C$_6$ alkyl, C$_5$ and C$_6$ cycloalkyl and phenyl; m is 2 to 14; y is 1 to 4; g times y is 1 to 6; and s is 1 to 3.

10. Complexes of claim 9, wherein y is 1 or 2.
11. Complexes of claim 10, wherein y is 2, g times y is 6 and s is 2.
12. Complexes of the formula $$([\phi_2 P(CH_2)_m]_2 Si(CH_3)_2)_3 [Rh(CO)H]_2$$

wherein m is 2 to 14.

13. Complexes of claim 12, wherein m is 2 to 3.
14. Complexes of the formula:

$$[(Ar_2PQ)_y SiR_{4-y}]_g (MX_n)_s$$

wherein Ar is an unsubstituted C$_6$–C$_{10}$ aromatic radical Q is an unsubstituted C$_1$ to C$_{30}$ saturated open chain alkylene radical; R is an unsubstituted C$_1$ to C$_{10}$ hydrocarbyl radical; M is a Group VIII transition metal selected from the group consisting of Co, Rh, Ir, Ru, X is an anion or organic ligand, excluding halogen, satisfying the coordination sites of the metal; y is 1 to 4; g is 1 to 6 with the proviso that g times y is 1 to 6; n is 2 to 6; and s is 1 to 3.

15. Complexes of the formula:

$$[(Ar_2PQ)_y SiR_{4-y}]_g [Rh(CO)H]_2$$

wherein Ar is an unsubstituted C$_6$ to C$_{10}$ aromatic radical; Q is an unsubstituted C$_1$ to C$_{30}$ saturated open chain alkylene radical; R is an unsubstituted C$_1$ to C$_{10}$ hydrocarbyl radical; y is 1 to 4; g times y is 1 to 6; n is 2 to 6; and s is 1 to 3.

16. Complexes of the formula:

$$[(Ar_2PQ)_y SiR_{4-y}]_g (MX_n)_s$$

wherein Ar is a substituted or unsubstituted C$_6$–C$_{10}$ aromatic radical, Q is a substituted or unsubstituted C$_1$ to C$_{30}$ saturated open chain alkylene radical, R is an unsubstituted or monosubstituted C$_1$ to C$_{10}$ hydrocarbyl radical, M is a Group VIII transition metal, selected from the group consisting of Co, Rh, Ir, Ru, Fe or Os, X is an anion or organic ligand, excluding halogen, satisfying the coordination sites of the metal, y is 1 to 4, g is 1 to 6 with the proviso that g times y is 1 to 6, n is 2 to 6, and s is 1 to 3, said substituents on said aromatic radical, on said alkylene radical and on said hydrocarbyl radical being chemically unreactive with materials used in and the products of hydroformylation reaction.

17. Complexes of claim 16 wherein M is Co, Rh, Ir, Ru.

18. Complexes of claim 17 wherein X is selected from the group consisting of H, CO and tertiary phosphine.

19. Complexes of claim 16 wherein s is 1, y is 1, g is 1 to 6.

20. Complexes of claim 19 wherein M is selected from the group consisting of Co, Rh, Ir and Ru; X is selected from the group consisting of H, CO, and tertiary phosphine.

21. Complexes of the formula $$(Ar_2PQSiR_3)_3RH(CO)H$$

wherein Ar is a substituted or unsubstituted $C_6$ to $C_{10}$ aromatic radical, Q is an unsubstituted or monosubstituted $C_1$ to $C_{30}$ open chain alkylene radical; and R is an unsubstituted or monosubstituted $C_1$ to $C_{10}$ hydrocarbyl radical, said substituents on said aromatic radical, on said alkylene radical and on said hydrocarbyl radical being chemically unreactive with materials used in and the products of a hydroformylation reaction.

22. Complexes of the formula $$[Ar_2PQSiR_3)_2Rh(CO)_3]^+[B(C_6H_5)_4]^-$$

wherein Ar is a substituted or unsubstituted $C_6$ to $C_{10}$ aromatic radical, Q is a substituted or unsubstituted $C_1$ to $C_{30}$ open chain alkylene radical, and R is an unsubstituted or monosubstituted $C_1$ to $C_{10}$ hydrocarbyl radical, said substituents on said aromatic radical, on said alkylene radical and on said hydrocarbyl radical being chemically unreactive with materials used in and the products of a hydroformylation reaction.

23. Complexes of the formula $$[\phi_2P(CH_2)_mSi(CH_3)_3]_3 \cdot RH(CO)H$$

wherein m is 1 to 4.

24. The complex of claim 23 wherein m is 2 or 3.

25. A complex of the formula $$[\phi_2PCH_2CH_2Si(CH_3)_3]_3 \cdot Rh(CO)H.$$

* * * * *